United States Patent

Wang

[11] Patent Number: 5,725,378
[45] Date of Patent: Mar. 10, 1998

[54] ARTIFICIAL TOOTH ASSEMBLY

[76] Inventor: Hong-Chi Wang, 58, Ma Yuan West St., Taichung, Taiwan

[21] Appl. No.: 689,712

[22] Filed: Aug. 16, 1996

[51] Int. Cl.⁶ ..................................................... A61C 8/00
[52] U.S. Cl. ............................................................. 433/173
[58] Field of Search ................................... 433/172, 173, 433/174, 175, 176; 606/72, 73

[56] References Cited

U.S. PATENT DOCUMENTS

| | | | |
|---|---|---|---|
| 3,497,953 | 3/1970 | Weissman | 433/173 |
| 4,523,587 | 6/1985 | Frey | 433/173 |
| 5,087,199 | 2/1992 | Lazarof | 433/173 |
| 5,489,210 | 2/1996 | Hanosh | 433/173 |

Primary Examiner—Nicholas D. Lucchesi

[57] ABSTRACT

An artificial tooth assembly has an artificial tooth crown and a denture base. The denture base comprises a cylinder seat, a plurality of plates, a threaded stud, a post and a hexagonal rod. The cylinder seat has a threaded hole, a plurality of longitudinal slots, and a plurality of transverse slots. Each longitudinal slot communicates with each corresponding transverse slot. An oblong hole is formed on each plate. A hexagonal recess hole is formed on the threaded stud. The post has a threaded lower portion and a mount. A hexagonal through hole is formed on the post. The plates are inserted in the corresponding transverse slots. A plurality of bolts are inserted in the corresponding longitudinal slots and the corresponding oblong holes to position the plates. The threaded stud is inserted in the cylinder seat. The threaded lower portion of the post is inserted in the cylinder seat. The hexagonal rod passes through the hexagonal through hole and the hexagonal recess hole. The artificial tooth crown is disposed on the post.

1 Claim, 2 Drawing Sheets

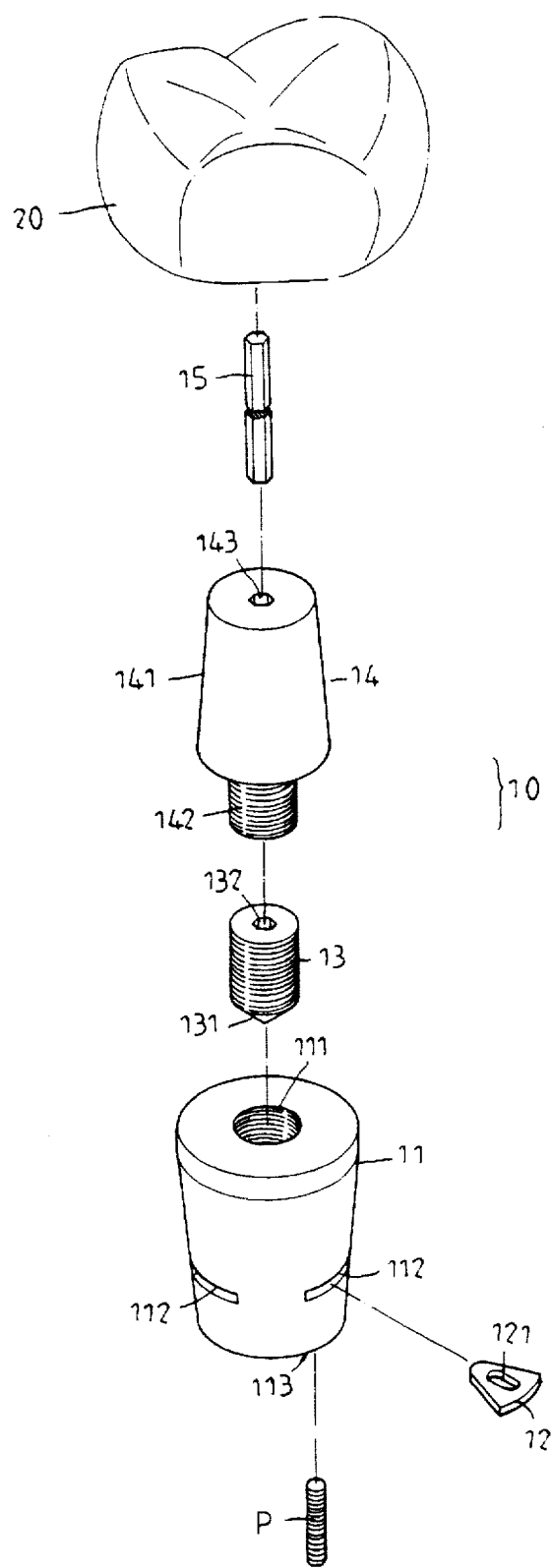
F I G. 1

ARTIFICIAL TOOTH ASSEMBLY

BACKGROUND OF THE INVENTION

The present invention relates to an artificial tooth assembly. More particularly, the present invention relates to a denture base which is made of titanium alloy.

The conventional denture implantation often drills a hole in an upper jawbone or a lower jawbone. An implant article is fixed on the hole. An abutment is locked on the implant article. An artificial tooth is disposed on the abutment. However, the artificial tooth, the abutment and the implant article may be pulled out if the thickness of the jaw bone of the user is very thin.

SUMMARY OF THE INVENTION

An object of the present invention is to provide an artificial tooth assembly which can be implanted on a jawbone securely.

Accordingly, an artificial tooth assembly has an artificial tooth crown and a denture base which is made of titanium alloy. The denture base comprises a cylinder seat, a plurality of plates, a threaded stud, a post and a hexagonal rod. The cylinder seat has a threaded hole formed on a longitudinal center of the cylinder seat, a plurality of longitudinal slots formed on a bottom of the cylinder seat, and a plurality of transverse slots formed on a periphery of the cylinder seat. Each of the longitudinal slots communicates with each of the corresponding transverse slots. An oblong hole is formed on each of the plates. A hexagonal recess hole is formed on a longitudinal center of the threaded stud. The threaded stud has a cone-shaped end. The post has a threaded lower portion and a truncated-cone mount connecting the threaded lower portion of the post. A hexagonal through hole is formed on a longitudinal center of the post passing through the truncated-cone mount and the threaded lower portion of the post. The plates are inserted in the corresponding transverse slots. A plurality of bolts are inserted in the corresponding longitudinal slots and the corresponding oblong holes to position the corresponding plates. The threaded stud is inserted in the cylinder seat via the threaded hole of the cylinder seat. The threaded lower portion of the post is inserted in the cylinder seat via the threaded hole of the cylinder seat to push the cone-shaped end of the threaded stud reaching a bottom end of the threaded hole of the cylinder seat. The hexagonal rod passes through the hexagonal through hole and the hexagonal recess hole to fasten the post and the threaded stud together. The artificial tooth crown has a lower recess hole formed on a lower center of the artificial tooth crown. It is an option to provide an adhesive coated on a periphery of the truncated-cone mount. The truncated-cone mount is inserted in the lower recess hole of the artificial tooth crown. The user can drill a hole on an upper jawbone or a lower jawbone. The cylinder seat is embeded in the drilled hole. The hexagonal rod is rotated by the user. The threaded stud and the post are driven by the hexagonal rod to move downward. Then the cone-shaped end of the threaded stud forces the plates to extend outward in the drilled hole. When the jawbone is grown to surround the plates, the cylinder seat will be positioned in the drilled hole securely. Then the artificial tooth crown is disposed on the post.

BRIEF DESCRIPTION OF THE DRAWINGS

FIG. 1 is a perspective exploded view of an artificial tooth assembly of a preferred embodiment in accordance with the present invention;

DETAILED DESCRIPTION OF THE INVENTION

Figure 3:
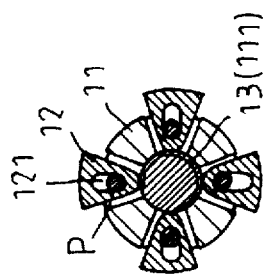
FIG. 3 is a sectional view taken along line 2A—2A in FIG. 2.

Referring to FIG. 1, an artificial tooth assembly comprises an artificial tooth crown 20 and a denture base 10 which is made of titanium alloy. The denture base 10 comprises a cylinder seat 11, a plurality of plates 12, a threaded stud 13, a post 14 and a hexagonal rod 15. The cylinder seat 11 has a threaded hole 111 formed on a longitudinal center of the cylinder seat 11, a plurality of longitudinal slots 113 formed on a bottom of the cylinder seat 11, and a plurality of transverse slots 112 formed on a periphery of the cylinder seat 11. Each of the longitudinal slots 113 communicates with each of the corresponding transverse slots 112. An oblong hole 121 is formed on each of the plates 12. A hexagonal recess hole 132 is formed on a longitudinal center of the threaded stud 13. The threaded stud 13 has a cone-shaped end 131. The post 14 has a threaded lower portion 142 and a truncated-cone mount 141 connecting the threaded lower portion 142 of the post 14. A hexagonal through hole 143 is formed on a longitudinal center of the post 14 passing through the truncated-cone mount 141 and the threaded lower portion 142 of the post 14.

Figure 2:
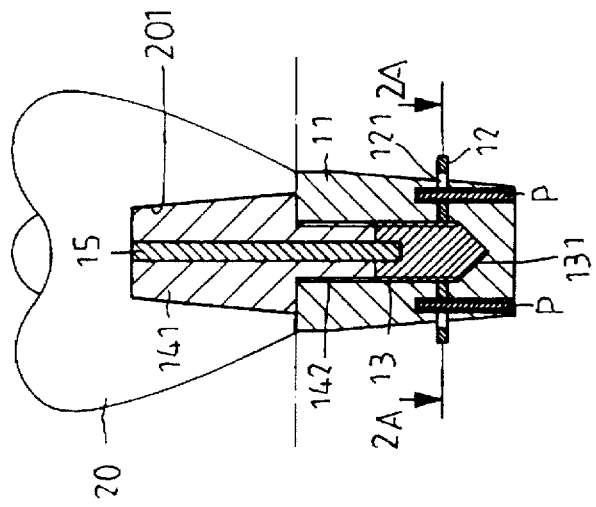
FIG. 2 is a sectional assembly view of FIG. 1 while a cone-shaped end of a threaded stud reaches a bottom end of a threaded hole of a cylinder seat.
Figure 5:
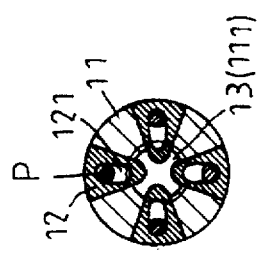
FIG. 5 is a sectional view taken along line 4A—4A in FIG. 4.
Figure 4:
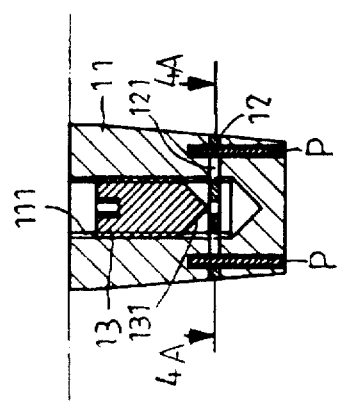
FIG. 4 is a partially sectional assembly view of an artificial tooth assembly while a cone-shaped end of a threaded stud does not reach a bottom end of a threaded hole of a cylinder seat.

Referring to FIGS. 1 to 5, the plates 12 are inserted in the corresponding transverse slots 112. A plurality of bolts P are inserted in the corresponding longitudinal slots 113 and the corresponding oblong holes 121 to position the corresponding plates 12. The threaded stud 13 is inserted in the cylinder seat 11 via the threaded hole 111 of the cylinder seat 11. The threaded lower portion 142 of the post 14 is inserted in the cylinder seat 11 via the threaded hole 111 of the cylinder seat 11 to push the cone-shaped end 131 of the threaded stud 13 reaching a bottom end of the threaded hole 111 of the cylinder seat 11. The hexagonal rod 15 passes through the hexagonal through hole 143 and the hexagonal recess hole 132 to fasten the post 14 and the threaded stud 13 together. The artificial tooth crown 20 has a lower recess hole 201, formed on a lower center of the artificial tooth crown 20. It is an option to provide an adhesive coated on a periphery of the truncated-cone mount 141. The truncated-cone mount 141 is inserted in the lower recess hole 201, of the artificial tooth crown 20.

The user can drill a hole on an upper jawbone or a lower jawbone. The cylinder seat 11 is embeded in the drilled hole. The hexagonal rod 15 is rotated by the user. The threaded stud 13 and the post 14 are driven by the hexagonal rod 15 to move downward. Then the cone-shaped end 131 of the threaded stud 13 forces the plates 12 to extend outward in the drilled hole. When the jawbone is grown to surround the plates 12, the cylinder seat 11 will be positioned in the drilled hole securely. Then the artificial tooth crown 20 is disposed on the post 14.

The invention is not limited to the above embodiment but various modification thereof may be made. Further, various changes in form and detail may be made without departing from the scope of the invention.

I claim:

1. An artificial tooth assembly comprising:

a denture base made of titanium alloy, said denture base comprising a cylinder seat, a plurality of plates, a threaded stud, a post and a hexagonal rod, said cylinder seat having a threaded hole formed on a longitudinal center of said cylinder seat, a plurality of longitudinal slots formed on a bottom of said cylinder seat, and a plurality of transverse slots formed on a periphery of said cylinder seat, each of said longitudinal slots communicating with each of said corresponding transverse slots, an oblong hole formed on each of said plates, a hexagonal recess hole formed on a longitudinal center of said threaded stud, said threaded stud having a cone-shaped end, said post having a threaded lower portion and a truncated-cone mount connecting said threaded lower portion of said post, a hexagonal through hole formed on a longitudinal center of said post passing through said truncated-cone mount and said threaded lower portion of said post, said plates inserted in said corresponding transverse slots, a plurality of bolts inserted in said corresponding longitudinal slots and said corresponding oblong holes to position said corresponding plates, said threaded stud inserted in said cylinder seat via said threaded hole of said cylinder seat, said threaded lower portion of said post inserted in said cylinder seat via said threaded hole of said cylinder seat to push said cone-shaped end of said threaded stud reaching a bottom end of said threaded hole of said cylinder seat, said hexagonal rod passing through said hexagonal through hole and said hexagonal recess hole to fasten said post and said threaded stud together, an artificial tooth crown having a lower recess hole formed on a lower center of said artificial tooth crown, and said truncated-cone mount inserted in said lower recess hole of said artificial tooth crown.

* * * * *